US00PP32202P2

(12) United States Plant Patent
Klemm et al.

(10) Patent No.: US PP32,202 P2
(45) Date of Patent: Sep. 15, 2020

(54) ***DIANTHUS* PLANT NAMED 'KLEDG19411'**

(50) Latin Name: ***Dianthus* sp.**
Varietal Denomination: KLEDG19411

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,808

(22) Filed: Jun. 10, 2019

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./263.1, 272, 273
See application file for complete search history.

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new *Dianthus* plant particularly distinguished by pink flowers with a red-purple border, very early flowering, and an upright habit, is disclosed.

1 Drawing Sheet

Genus and species: *Dianthus* sp.
Variety denomination: 'KLEDG19411'.

BACKGROUND OF THE NEW PLANT

The present invention comprises a new and distinct variety of *Dianthus*, botanically known as *Dianthus* sp., and hereinafter referred to by the variety name 'KLEDG19411'. 'KLEDG19411' originated from a spontaneous whole plant mutation in a greenhouse of the commercial variety 'KLEDG12163' (U.S. Plant Pat. No. 24,707) found in May 2016 in Japan.

In September 2016, 'KLEDG19411' was first vegetatively propagated by vegetative cuttings in Stuttgart Germany. 'KLEDG19411' was found to reproduce true to type in successive generations of asexual propagation in Latina, Italy via vegetative stem cuttings.

SUMMARY

The following are the most outstanding and distinguishing characteristics of this new variety when grown under normal horticultural practices in Stuttgart, Germany.

1. Pink flowers with a red-purple border;
2. Very early flowering; and
3. An upright habit.

DESCRIPTION OF THE PHOTOGRAPH

This new *Dianthus* plant is illustrated by the accompanying photograph of a plant approximately 5 months old and grown in a plastic greenhouse in Latina, Italy. The photographs were taken in March 2019. The colors shown are as true as can be reasonably obtained by conventional photographic procedures.

DESCRIPTION OF THE NEW VARIETY

Figure 1:
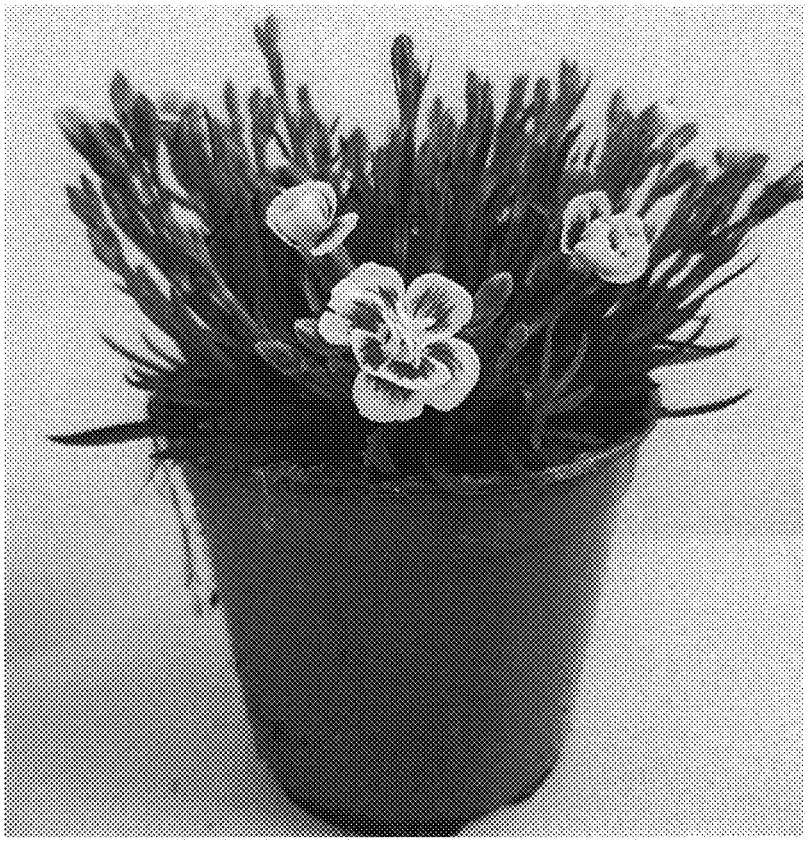
FIG. 1 shows the whole plant grown in a pot.
Figure 2:
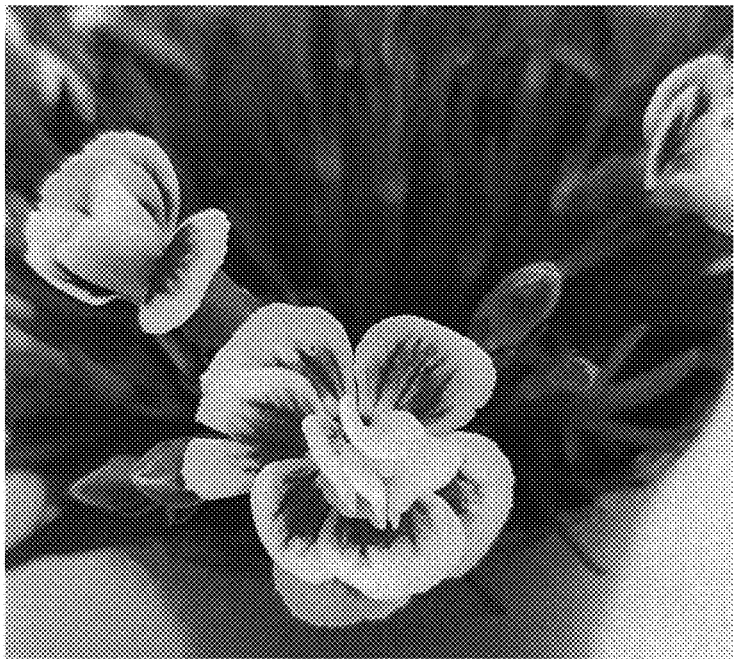
FIG. 2 shows a close up image of the flowers, buds, and foliage of the plant.

The following detailed descriptions set forth the distinctive characteristics of 'KLEDG19411'. The data which define these characteristics were collected from asexual reproductions carried out in Latina, Italy. Data was collected in March 2019 on 5 month old plants propagated and grown in a plastic greenhouse under cold conditions. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* sp.
- *Common*.—Perennial carnation.
- *Designation*.—'KLEDG19411'.

Parentage: Spontaneous whole plant mutation of 'KLEDG12163' (U.S. Plant Pat. No. 24,707).

Plant:
- *Plant form*.—Upright.
- *Plant height*.—6.0 cm to 8.0 cm.
- *Plant diameter or spread*.—12.0 cm to 15.0 cm.
- *Propagation type*.—Vegetative cuttings, stem cutting.
- *Time to produce a rooted young plant*.—10 to 14 days.
- *Root description*.—White and fine.
- *Rooting habit* (*shape*).—Lanceolate.

Lateral branches:
- *Number of lateral branches per plant*.—2 to 5.
- *Strength*.—Moderate to strong.
- *Length*.—5.0 cm to 6.0 cm.
- *Diameter*.—1.8 cm to 2.3 cm.
- *Internode length*.—0.2 cm to 1.0 cm.
- *Number of internodes per branch/stem*.—3 to 5.
- *Node length*.—0.2 cm to 0.4 cm.
- *Node diameter*.—0.2 cm to 0.4 cm.
- *Texture*.—Smooth.
- *Color*.—RHS 146B (Yellow-Green).
- *Branch/stem appearance*.—Solid.

Foliage:
- *Arrangement*.—Opposite.
- *Length*.—4.0 cm to 5.0 cm.
- *Width*.—0.3 cm to 0.5 cm.
- *Shape*.—Lanceolate.
- *Apex*.—Acute.

*Base*.—Obtuse.
*Margin*.—Entire.
*Texture* (*both upper and lower surfaces*).—Smooth.
*Immature leaf color* (*both surfaces*).—RHS 138A (Green).
*Mature leaf color* (*both surfaces*).—RHS 137A (Green).
*Venation pattern*.—Absent.
*Leaf attachment*.—Sessile.

Flowers:
*Flower type and habit*.—Semi-double, small sprays, round.
*Fragrance*.—Present, gentle sweet carnation fragrance.
*Natural flowering season*.—Spring to fall.
*Position of flowers relative to the foliage*.—Moderately above.
*Number of flowers per spray*.—3 to 5.
*Diameter of the inflorescence/spray* (*with 3-5 flowers*).—5.0 cm to 7.0 cm.
*Flower longevity on the plant*.—14 to 18 days.
*Buds*.—Length: 0.5 cm to 1.5 cm. Diameter: 0.3 cm to 0.4 cm. Shape: Elliptic. Color: RHS 138A (Green). Extrusion of the styles at the bud stage: Absent.
*Corolla*.—Quantity of petals and arrangement: 7 to 12 in several whorls. Corolla height: 0.8 cm to 1.5 cm. Corolla diameter: 1.5 cm to 2.5 cm. Petal length: 1.8 cm to 2.5 cm. Petal width: 1.0 cm to 1.2 cm. Petal shape: Spoon-shaped. Petal apex: Obtuse. Petal base: Acute. Petal margin: Serrated. Depth of petal margin: Shallow. Petal texture (both upper and lower surfaces): Smooth. Petal luster (both surfaces): Soft. Petal color: Immature: Upper surface: RHS 77A (Purple) with RHS 155A (White) at margins. Lower surface: RHS 155A (White). Mature: Upper surface: RHS 77A (Purple) with RHS 155A (White) at margins. Lower surface: RHS 155A (White).
*Calyx*.—Quantity of sepals and arrangement: Composed of 5 sepals fused at the base. Shape: Campanulate. Calyx height: 0.8 cm to 1.5 cm. Calyx diameter (at the apex): 0.4 cm to 0.6 cm. Sepal texture (both upper and lower surfaces): Smooth. Sepal color: Upper surface: RHS 137A (Green). Lower surface: RHS 137D (Green). Sepal length: 0.8 cm to 1.3 cm. Sepal diameter: 0.3 cm to 0.5 cm. Sepal apex: Acute. Sepal base: Obtuse. Sepal margin: Smooth. Sepal luster (both surfaces): Soft.

Peduncles:
*Length*.—5.0 cm to 8.0 cm.
*Diameter*.—0.2 cm.
*Strength*.—Moderate.
*Texture*.—Smooth.
*Color*.—RHS 146B (Green).

Reproductive organs:
*Stamens*.—Quantity per flower: Moderate, 5 to 7. Filament length: 0.8 cm to 1.0 cm. Filament color: RHS 157B (Green-White). Anther length: 0.1 cm. Anther diameter: 0.05 cm. Anther color: RHS N155B (White). Pollen amount: Absent.
*Pistils*.—Not observed.

Fruit and seed set: None observed.

Disease and pest/insect resistance: No disease and pest/insect resistance observed.

COMPARISON WITH PARENTAL LINE AND KNOWN VARIETY

'KLEDG19411' is distinguished from its parent as described in Table 1.

TABLE 1

Comparison with Parental Line

| Characteristic | 'KLEDG19411' | 'KLEDG12163' |
|---|---|---|
| Main flower color | RHS 77A (Purple) | RHS 75B (Purple) |
| Secondary flower color | RHS 155A (White) | RHS 71A (Red-Purple) |

'KLEDG19411' can be compared to the commercial *Dianthus* variety 'Peach Party', also known as 'KLEDG18305' (U.S. Plant Pat. No. 31,019). Differences between the varieties are described in Table 2.

TABLE 2

Comparison with Similar Variety

| Characteristic | 'KLEDG19411' | 'KLEDG18305' |
|---|---|---|
| Flower type | Semi-double | Single |
| Flower color | Purple with white border and eye | Pink with purple ring |
| Flowering time | Very early | Early to medium |

We claim:

1. A new and distinct variety of *Dianthus* plant designated 'KLEDG19411' as illustrated and described herein.

* * * * *